United States Patent
Byun et al.

(10) Patent No.: US 9,598,353 B2
(45) Date of Patent: Mar. 21, 2017

(54) PROCESS FOR THE RACEMIZATION OF α-AMINO ACIDS

(71) Applicant: Aminologics Co., Ltd., Gangnam-gu, Seoul (KR)

(72) Inventors: Il Suk Byun, Seongnam-si (KR); Kyu Sung Han, Seoul (KR); Hye Rim Ga, Seoul (KR)

(73) Assignee: Aminologics Co., Ltd., Seoul (KR)

(*) Notice: Subject to any disclaimer, the term of this patent is extended or adjusted under 35 U.S.C. 154(b) by 0 days.

(21) Appl. No.: 14/913,979

(22) PCT Filed: Aug. 7, 2014

(86) PCT No.: PCT/KR2014/007320
§ 371 (c)(1),
(2) Date: Feb. 23, 2016

(87) PCT Pub. No.: WO2015/026082
PCT Pub. Date: Feb. 26, 2015

(65) Prior Publication Data
US 2016/0221929 A1  Aug. 4, 2016

(30) Foreign Application Priority Data
Aug. 23, 2013  (KR) ........................ 10-2013-0100219

(51) Int. Cl.
*C07C 227/36* (2006.01)
*B01J 31/22* (2006.01)

(52) U.S. Cl.
CPC ......... *C07C 227/36* (2013.01); *B01J 31/2295* (2013.01); *B01J 2231/50* (2013.01); *B01J 2531/16* (2013.01)

(58) Field of Classification Search
CPC . C07C 227/36; B01J 31/2295; B01J 2231/50; B01J 2531/16
See application file for complete search history.

(56) References Cited

U.S. PATENT DOCUMENTS

| | | |
|---|---|---|
| 2,586,154 A | 2/1952 | Emmick |
| 3,213,106 A | 10/1965 | Sasaji et al. |
| 4,401,820 A | 8/1983 | Chibata et al. |
| 4,766,250 A | 8/1988 | Mirviss |
| 4,769,486 A | 9/1988 | Harada et al. |

FOREIGN PATENT DOCUMENTS

| | | |
|---|---|---|
| EP | 0937705 A2 | 8/1999 |
| JP | 11228512 A | 8/1999 |
| JP | 1999322684 A | 11/1999 |
| KR | 198600339 B1 | 4/1986 |
| KR | 2010106221 A | 10/2010 |
| KR | 2013100219 A | 9/2013 |
| KR | 2015022411 A | 3/2015 |
| KR | 1561828 B1 | 10/2015 |
| WO | 2015026082 A1 | 2/2015 |

OTHER PUBLICATIONS

Rajesh et al, Dalton Transactions, 2014, 43(34), 12952-12960.*
Weinstein et al, Inorganic Chemistry, 1970, 9(9), 2104-2112.*
International Search Report and Written Opinion dated Nov. 19, 2014, regarding Korean Application No. KR2014-007320, and English translation.
International Preliminary Report on Patentability dated Feb. 23, 2016, and Written Opinion dated Nov. 19, 2014, regarding Korean Application No. KR2014-007320, and English translation.
Makoto Ando: "Catalytic Activities of Salicylaldehyde Derivatives. VIII. Kinetic Studies of the Catalytic Racemization of L-Glutamic Acid at 25° C.," The Institute of Physical and Chemical Research, Wako-shi, Saitama 351 (Received Jan. 10, 1978), Bulletin of the Chemical Society of Japan, vol. 51 (8), 2366-2368 (1978).
Notice of Grounds for Rejection dated May 12, 2015, regarding Korean Application No. KR10-2013-0100219, and English translation.
R.B. Johns, D.J. Whelan: "Synthesis of Deuterated Amino Acids", Australian Journal of Chemistry, vol. 19, 2143 (1966).
Makoto Ando: "Catalytic Activities of Salicylaldehyde Derivatives. II, Kinetic Studies of the Racemization of Amino 4cid," The Institute of Physical and Chemical Research, Yamato-machi, Kitaadachi-gun, Saitama (Received Feb. 14, 1969), Bulletin of the Chemical Society of Japan, vol. 42 (9), 2628-2631 (1969).
Ming-Daw Tsai; Herschel J.R. Weintraub, etal: "Conformation-Reactivity Relationship for Pyridoxal Schiff's Bases. Rates of Racemization and z-Hydrogen Exchange of the Pyridoxal Schiff's Bases of Amino Acids", vol. 17, No. 16, 1978, p. 3183.

* cited by examiner

*Primary Examiner* — Shailendra Kumar
(74) *Attorney, Agent, or Firm* — Arent Fox LLP

(57) ABSTRACT

According to the present invention, a method is provided wherein a basic aqueous phase containing an optically active α-amino acid is brought into contact with an organic phase containing a racemisation catalyst in the form of a copper metal complex of copper ions and an α-amino acid and salicylaldehyde, in the presence of a phase transition catalyst, thereby subjecting the optically active α-amino acid to racemisation. In the α-amino acid racemisation method according to the present invention, the reaction conditions are mild and thus there is little α-amino acid breakdown and the yield is high, the racemisation catalyst can be reused, the α-amino acid resulting from the racemisation can easily be isolated and purified, and the racemisation method can be implemented in volume such that the invention is economic.

7 Claims, No Drawings

PROCESS FOR THE RACEMIZATION OF α-AMINO ACIDS

CROSS REFERENCE TO RELATED APPLICATION

This application is a 35 U.S.C 371 National Phase Application No. PCT/KR2014/007320 filed Aug. 6, 2014, which claims priority to Korean Application No. 10-2013-0100219 filed Aug. 23, 2013, the disclosure of these prior applications are hereby incorporated in their entirety by reference.

TECHNICAL FIELD

The present invention relates to a method for the racemization of α-amino acids, in particular a method for the racemization of α-amino acids comprising contacting an organic phase containing a racemization catalyst with an aqueous basic solution containing an optically active α-amino acid in the presence of a phase transfer catalyst.

BACKGROUND ART

In the production of optically active D- or L-α-amino acids used as a raw material or intermediate, etc. in the field of pharmaceuticals, agriculture and fine chemistry, the amino acid having optical activity may be directly prepared as an optically active isomer with the desired optical activity or, it may be prepared as an optically active isomer having the desired optical activity by preparing a racemic mixture and then subjecting it to an optical resolution method.

In the process of producing D- or L-α-amino acids by an optical resolution of racemic amino acids, the remaining optical isomers after the optical resolution may usually be subjected to racemization process and then reused as racemic mixtures for an optical resolution for economic reasons.

Recently, L-amino acid or D-amino acid can be mass-produced by chemical methods or biological methods. In case where such mass-produced L-amino acid or D-amino acid is inexpensive but the L-amino acid or D-amino acid having an opposite steric structure is expensive, the racemization of amino acids may be an important key technology whereby an amino acid having an inexpensive steric structure is transformed to an amino acid having an expensive steric structure.

As a racemization method of α-amino acid having optical activity, several methods including chemical and biological methods have been disclosed.

U.S. Pat. Nos. 2,586,154 and 4,769,486 disclose a chemical racemization method wherein α-amino acid is introduced in a strong acid or alkaline aqueous solution and subjected to a racemization at a high temperature. In the methods of these documents, the severe reaction conditions (high temperature, long reaction period) may cause decomposition of α-amino acid and thus many side products are generated. [See Advances in Protein Chemistry, Vol. 4, p. 4339 (1948)].

As an improved version of the above-described chemical method, U.S. Pat. No. 3,213,106 (1965) has proposed a racemization method wherein α-amino acid is introduced in a closed vessel and subjected to a racemization at a high temperature (100~150° C.). The method has problems that the reaction temperature is very high above the boiling point of water and thus the reactor needs to be a closed vessel that can endure the high pressure.

As a further improved method of the above-described chemical method, U.S. Pat. No. 4,401,820 (1983) discloses a racemization method wherein the racemization is more easily carried out at a temperature of 100° C. or less by using organic acids such as formic acid, acetic acid, propionic acid instead of water as a solvent and employing a variety of aldehydes as a catalyst. However, there are problems that the organic acid used as a solvent has a bitter smell and toxicity and thus requires a complicated process for its use and recovery.

Japanese Patent Laid-Open Publications H11-228512 and H11-322684 (corresponding to European Patent Publication EP 0937705A) disclose a catalytic racemization method wherein a racemization of α-amino acid is carried out by using salicylaldehyde as a catalyst under an acidic condition. In the method of these documents, the yield of α-amino acid is low due to severe reaction conditions.

Meanwhile, it has been known that a Schiff base obtained by reacting salicylaldehyde or substituted salicylaldehyde with α-amino acid is combined with a copper ion (Cu2+) to give a copper metal complex (Cu-Metal Complex), which can be utilized as a very useful racemization catalyst (Scheme 1). [Bulletin of the Chemical Society of Japan, Vol 51 (8), 2366 (1978); Biochemistry, Vol 17 (16) 3183 (1978); Inorganic Chemistry, Vol 9 (9), 2104 (1970); Bulletin of the Chemical Society of Japan, Vol 42 (9), 2628 (1969); Australian Journal of Chemistry, Vol 19, 2143 (1966)].

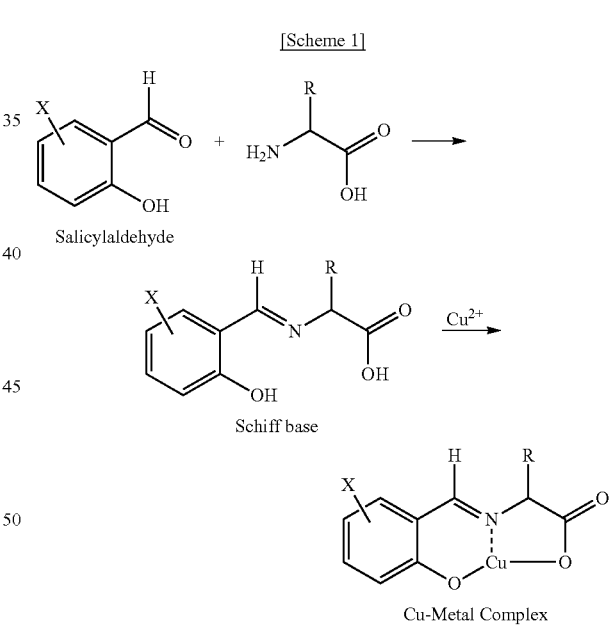

The above Cu-metal complex is easy to prepare and is useful as a racemization catalyst since a variety of amino acids can be racemized at the normal temperature even with a small amount under a basic condition in a water solvent. However, the above Cu-metal complex has problems that, when the resultant reaction mixture is acidified in order to isolate racemic α-amino acid, the Cu-metal complex catalyst may be decomposed and thus cannot be recycled and that the salicylaldehyde and copper ion which result from decomposition should be removed during the separation and purification step of α-amino acid.

DETAILED DESCRIPTION OF THE INVENTION

Technical Problem

The present inventors have studied the existing racemization method of α-amino acids employing copper metal complex as a racemization catalyst and tried to develop an improved way for carrying out the existing racemization method more easily and economically and for reusing the catalyst of copper metal complex without decomposition.

Technical Solution

The present inventors have found that, when contacting an organic phase containing a copper metal complex as a racemization catalyst with an aqueous phase containing α-amino acid or stirring a two-phase mixture containing them in the presence of a phase transfer catalyst, first, the racemization of α-amino acid can be performed under relatively mild conditions, second, the organic phase and the aqueous phase can be easily separated after the completion of the racemization reaction, third, the organic phase containing the catalyst of copper metal complex can be reused without a decrease of the catalytic activity, forth, the racemized α-amino acid can be easily isolated and purified since the aqueous phase containing racemized α-amino acid does not contains other reactant, and thus, that it is possible to carry out the racemization of α-amino acid in a large scale and at a low cost. As a result, the present inventors have completed the present invention.

Effects of the Invention

The racemization method of α-amino acid according to the present invention has a high yield due to the mild reaction conditions which result in less decomposition of α-amino acid; allows to recycle the racemization catalyst; enables easy separation and purification of the racemized α-amino acid; and has an economic advantage due to its mass production capability.

Best Mode for Carrying Out the Invention

The object of the present invention is to provide a method for racemization of α-amino acid which comprises contacting an organic phase containing copper metal complex composed of salicylaldehyde, α-amino acid and copper ion as a racemization catalyst with an aqueous basic phase containing an optically active α-amino acid in the presence of a phase transfer catalyst.

According to the present invention, said copper metal complex can be represented by the following Chemical Formula 1.

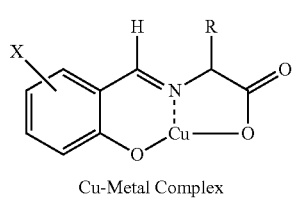

[Formula 1]

Cu-Metal Complex wherein, X represents a hydrogen, a halogen atom such as chloro or bromo, an alkyl group having from 1 to 4 carbon atoms, an alkoxy group having from 1 to 4 carbon atoms or a nitro group, preferably 5-nitro group.

The copper-metal complex (Cu-Metal Complex) of Formula 1 which can be used as a racemization catalyst can be prepared by known methods. For example, the copper metal complex of Formula 1 can be prepared by reacting alicylaldehyde or its derivatives with amino acid to form a Schiff base and having copper ion coordinated thereto.

The salicylaldehyde derivative may have one or more diverse substituents on its phenyl ring. By way of examples of the substituents, mention can be made to a halogen atom such as F, Cl or Br, an alkyl group having 1 to 4 carbon atoms such as methyl, ethyl, propyl or butyl, and an alkoxy group having 1 to 4 carbon atoms such as methoxy, ethoxy, propoxy or butoxy and a nitro group (NO2). Preferably mention can be made of 5-nitrosalicylaldehyde.

α-Amino acids to which the racemization of the present invention can be applied can encompass both of natural and non-natural amino acids, unless otherwise specified. As examples of the α-amino acid to which the racemization method of the present invention can be preferably applied, mention can be made of phenylalanine, substituted phenylalanine, leucine, alanine and methionine, preferably phenylalanine, 4-chlorophenylalanine and leucine.

In the present invention, α-amino acid is not specifically restricted with respect to its stereo-structure if the α-amino acid has an optical activity. It is possible to employ not only an optically active α-amino acid such as D-α-amino acid and L-α-amino acid but also an α-amino acid mixture having optical activity wherein any one of D-α-amino acid and L-α-amino acid is present in excess or predominantly.

In the context of the present invention, therefore, the term "an optically active α-amino acid" means any one of D-α-amino acids and L-α-amino acids, and the term "α-amino acid (mixture) having optical activity" means not only an optically active α-amino acid such as D-α-amino acid or L-α-amino acid but also a mixture of α-amino acid stereoisomers, wherein said mixture has an optical activity since any one of D-α-amino acid and L-α-amino acid is present in excess or predominantly. But said terms are not strictly employed.

In the present invention, the phase transfer catalyst can be selected from a quaternary ammonium salt of general formula R4N+X− or quaternary phosphonium salt of general formula of R4P+X−, wherein R independently represents an alkyl group having 1~20 carbon atoms, a substituted or unsubstituted phenyl group or a substituted or unsubstituted benzyl group, and X represents Cl, Br, I or OH. For example, mention can be made of tetrabutylammonium chloride, cetyl trimethylammonium bromide, benzyl trimethylammonium chloride, Aliquat 336 (commercial name), tetraphenylphosphonium hydroxide, or the like.

According to a preferred embodiment of the present invention, the phase transfer catalyst is selected from tetraalkylammonium halides, and specifically, mention can be made of Aliquat 336.

According to one embodiment of the present invention, the racemization method of the α-amino acid may specifically comprise the following steps:

(A) preparing an organic phase containing the above copper metal complex of the chemical formula (1) and the above phase transfer catalyst, (B) preparing a basic aqueous phase comprising an optically active α-amino acid and an alkaline compound, (C) vigorously stirring a two-phase mixture obtained by combining the organic phase and the aqueous phase at a temperature 10 to 80° C., specifically at 20 to 70° C., preferably 30 to 60° C. for 1 to 40 hours, specifically 2 to 35 hours, preferably 3 to 30 hours, (D) optionally, separating the racemized amino acid from the aqueous phase separated in a layer, (E) optionally, allowing the above-resultant two-phase mixture to stand to separate an organic phase and an aqueous phase into layers, (F) optionally, employing the organic phase separated in a layer again in step (a).

According to yet another embodiment of the invention, the racemization method of α-amino acids can comprise (1) a step for preparing an organic phase comprising a copper metal catalyst [step (A)], (2) steps for carrying out a racemization of optically active α-amino acid [steps (B) and (C)], (3) steps for recovering the racemized α-amino acid [steps (D) and (E)], and (4) a step for recycling the racemization catalyst [step (F)].

Below, detailed descriptions are provided for the step (1) for preparing an organic phase containing a catalyst of copper metal complex [Step (A)], and for the step (2) of carrying out a racemization of an optical active α-amino acid [Steps (B) and (C)].

(1) Preparation of a Catalyst of Copper Metal Complex and an Organic Phase Comprising the Same:

According to a preferred embodiment of the present invention, an organic phase comprising the above copper metal complex and the above phase transfer catalyst can be obtained by the method comprising the following steps:

(a-1) preparing an organic phase comprising salicylaldehyde and a phase transfer catalyst, (a-2) preparing a basic aqueous phase comprising α-amino acid, an alkali compound and a copper salt compound, (a-3) stirring a two-phase mixture of the organic phase and the aqueous phase, (a-4) allowing the resultant two-phase mixture to stand to separate an organic phase into a layer.

First, in step (a-1), an organic phase is prepared by adding salicylaldehyde or its derivative (e.g., 5-nitrosalicylaldehyde) and a phase transfer catalyst (e.g. Aliquat 336) into an organic solvent such as dichloromethane (CH2Cl2).

In step (a-2), a basic aqueous phase is prepared by dissolving an optically active α-amino acid and/or a racemic α-amino acid (e.g. phenylalanine) in distilled water; adding sodium hydroxide into the resultant aqueous solution to make it alkaline; and adding a copper salt compound into the resultant basic aqueous solution.

In step (a-3), a two-phase mixture of the above organic phase and the above basic aqueous phase is stirred to contact the organic phase and the aqueous phase, so that the amino acid and copper ion are transferred into the organic phase by the phase transfer catalyst. Then, in the organic phase, salicylaldehyde, amino acid and copper ions will form a Schiff base according to the process shown in Scheme 1, and then form a copper metal complex.

In step (a-4), the resultant two-phase mixture is allowed to stand so that a layer separation of an aqueous phase and an organic phase occurs, and then the organic layer is separated, for example, by using a separating funnel. Since the resultant organic phase contains copper metal complex of Formula 1 and a phase transfer catalyst, it will be used as "an organic phase containing a catalyst of copper metal complex" in the next racemization step.

Organic solvents which can be used for an organic phase in the step for forming a copper metal complex is not particularly limited, but mention can be made of, for example, dichloromethane, dichloroethane and chloroform.

As examples of the alkali compound, mention can be made of an alkali metal hydroxide or alkaline earth metal hydroxide, specifically, lithium hydroxide, sodium hydroxide, potassium hydroxide, calcium hydroxide, and magnesium hydroxide. The amount of the alkali compound is not particularly limited, but it may be added in an amount of 0.9 to 2.0 equivalents, specifically 0.9 to 1.5 equivalents, preferably 1.0 to 1.2 equivalents, with respect to the α-amino acid.

As a source of copper ions, it is possible to use a variety of copper salts, and mention can be specifically made of copper salt compounds containing divalent copper ion, for example, copper chloride (CuCl2), copper sulfate (CuSO4), copper acetate (Cu(OAc)2), or the like.

(2) Racemization of an Optical Active α-Amino Acid:

The racemization of an optically active α-amino acid can be carried out by contacting an organic phase [prepared in step (A)] containing copper metal complexes and the above-described phase transfer catalyst with a basic aqueous phase [prepared in Step (B)] containing an optically active α-amino acid and an alkali compound.

In the above step (B), the basic aqueous phase can be prepared by adding α-amino acid and an alkali compound such as sodium hydroxide into water. α-Amino acids can be used in an amount of 1 to 50 equivalents, in particular 2 to 30 equivalents, preferably 5 to 20 equivalents with respect to salicylaldehyde derivatives of the above organic phase, and the alkali compound can be added in an amount of 0.9 to 2.0 equivalents, specifically 0.9 to 1.5 equivalents, preferably 1.0 to 1.2 equivalents with respect to α-amino acid.

In the above step (C), the contact of an aqueous phase and an organic phase can be carried out by combining the aqueous phase and the organic phase to form a two-phase mixture, which is then stirred at or around the normal temperature, generally at a temperature of 10 to 80 ° C., specifically 20 to 70 ° C., preferably 30 to 60 ° C. for a period of 1 to 40 hours, specifically 2 to 35 hours, preferably 3 to 30 hours. If the reaction temperature is high, the copper metal complex may be slightly decomposed to reduce the racemization velocity. If the reaction temperature is low, there is a tendency the racemization velocity decreases.

In said step (D), when the resultant two-phase mixture is allowed to stand, the organic phase and the aqueous phase are separated and each of them can be obtained by using a separating funnel or the like. From the resultant aqueous phase, the racemized amino acid can be isolated and purified. The resultant organic phase can be recycled as a racemization catalyst, specifically reused as an organic phase in the above step (A). In such case, it is possible to further add the catalyst of copper metal complex and/or the phase transfer catalyst, if necessary. It has been confirmed that, according to the present invention, an organic phase containing the catalyst of copper metal complex can maintain its catalytic activity even after use in at least 5 times of racemization.

As organic solvents that can be employed as the organic phase in the racemization step, mention can be made of organic solvents which have been employed as an organic phase in the manufacturing step of copper metal complex, and preferably of dichloromethane.

According to the present invention, since the racemization of α-amino acid can be carried out under mild conditions, the decomposition of α-amino acid hardly occurs, and accordingly the yield of α-amino acid is high. In addition, since the organic phase is separated from the aqueous phase after the completion of racemization of α-amino acid, the organic phase containing copper metal complex can be reused at least 5 times without a decrease of catalytic activity. Since the aqueous phase containing racemized α-amino acid almost does not contain copper metal complex, copper ions and salicylaldehyde or the like, it is easy to isolate and purify α-amino acid. Therefore, according to the present invention, it is possible to economically perform the racemization of an optically active α-amino acid on a large scale.

Below, the present invention will be described in detail by examples. However, the examples are given for the purpose of illustrating the invention in more detail and do not restrict the scope of the present invention. The following examples can be appropriately modified or altered by a skilled person having an ordinary knowledge within the scope of the invention.

Example 1

Racemization of L-phenylalanine (1) Preparation of an Organic Layer Containing Copper Metal Complex In dichloromethane 120 mL, 5-nitrosalicylaldehyde (10.0 g, 59.8 mmol) and Aliquat 336 (33.9 g, 83.9 mmol) were dissolved to give an organic phase. In distilled water 100 ml, racemic phenylalanine (19.8 g, 119.9 mmol), sodium hydroxide (5.75 g, 144 mmol) and copper chloride (CuCl2) (1.6 g, 11.9 mmol) were dissolved to give an aqueous phase. The organic phase and the aqueous phase were mixed, the resultant two-phase mixture was vigorously stirred for 2 hours, followed by a phase separation to give an organic layer containing copper metal complex.

(2) Racemization

In distilled water 500 ml, L-phenylalanine (98.8 g, 598 mmol) and sodium hydroxide (28.7 g, 718 mmol) were dissolved to give an aqueous phase, to which the organic layer obtained in the above step 1) was introduced. The resultant two-phase mixture was stirred at 25° C. for 12 hours, followed by a phase separation to give an aqueous layer. The aqueous layer was analyzed with a chiral column (Chirosil RCA) and it was confirmed that L/D ratio of phenylalanine is 50.2/49.8 and thus a racemization has occurred.

[Conditions for the Chiral HPLC Analysis]
Column: Chirosil RCA 5 uM×25 Cm
Mobile phase: 10 mM HClO4 50% in MeOH
Velocity of mobile phase: 0.5 mL/min
Column temperature: 40° C.

Examples 2~5

Racemization of L-phenylalanine

In the same manner as in Example 1, step 1) and step 2) were performed to proceed a racemization of phenylalanine.

The racemization results of Examples 1-5 are shown in Table 1 below:

TABLE 1

| Examples | Reaction time | L/D ratio |
|---|---|---|
| 1 | 12 h | 50.1/49.8 |
| 2 | 12 h | 50.1/49.9 |
| 3 | 16 h | 50.0/50.0 |
| 4 | 15 h | 51.5/45.5 |
| 5 | 16 h | 51.0/49.0 |

Example 6

Racemization of L-phenylalanine

1) Preparation of an Organic Layer Containing Copper Metal Complex

In dichloromethane 70 mL, 5-nitrosalicylaldehyde (5.0 g) and Aliquat 336 (17 g) were dissolved to give an organic phase. In distilled water 50 ml, L-phenylalanine (10 g), sodium hydroxide (2.9 g) and copper chloride (CuCl2) (0.8 g) were dissolved to give an aqueous phase. The organic phase and the aqueous phase were mixed and the resultant two-phase mixture was vigorously stirred for 2 hours, followed by a phase separation to obtain an organic layer containing copper metal complex.

2) Racemization

In distilled water 260 ml, L-phenylalanine (50 g) and sodium hydroxide (14.5 g) were dissolved to give an aqueous phase, to which the organic layer obtained in the above step 1) was introduced. The resultant two-phase mixture was stirred at 25° C. for 12 hours, followed by a phase separation to give an aqueous layer. The aqueous layer was analyzed with a chiral column (Chirosil RCA) and it was confirmed that a racemization has occurred.

Example 7

Racemization of L-phenylalanine

1) Preparation of an Organic Layer Containing Copper Metal Complex

In dichloromethane 115 mL, salicylaldehyde (7.3 g) and Aliquat 336 (33.6 g) were dissolved to give an organic phase. In distilled water 100 ml, racemic phenylalanine (19.8 g), sodium hydroxide (5.75 g) and copper sulfate (CuSO4) (1.9 g) were dissolved to give an aqueous phase. The organic phase and the aqueous phase were mixed and the resultant two-phase mixture was vigorously stirred for 2.5 hours, followed by a phase separation to obtain an organic layer containing copper metal complex.

2) Racemization

In distilled water 500 ml, L-phenylalanine (98.8 g) and sodium hydroxide (28.7 g) were dissolved to prepare an aqueous phase, to which the organic phase obtained in the above step 1) was added. The resultant two-phase mixture was stirred for 13 hours at 25° C., followed by phase separation to give an aqueous layer. The aqueous layer was analyzed by a chiral column (Chirosil RCA) and it was confirmed that L/D ratio of phenylalanine is 50.8/49.2 and thus a racemization has occurred.

Example 8

Racemization of L-4-chlorophenylalanine

1) Preparation of an Organic Layer Containing Copper Metal Complex

In dichloromethane 130 mL, 5-nitrosalicylaldehyde (10.0 g) and Aliquat 336 (33.9 g) were dissolved to prepare an organic phase. In distilled water 150 ml, racemic 4-chlorophenylalanine (24.0 g), sodium hydroxide (5.77 g) and copper chloride (CuCl2) (1.4 g) were dissolved to prepare an aqueous phase. The organic phase and the aqueous phase were mixed and the resultant two-phase mixture was vigorously stirred for 2 hours, followed by phase separation to obtain an organic layer containing copper metal complex.

2) Racemization

In distilled water 700 ml, L-4-chlorophenylalanine (120 g) and sodium hydroxide (28.0 g) were dissolved to prepare an aqueous phase, to which the organic layer obtained in the above step 1) was added. The resultant two-phase mixture was stirred at 30° C. for 13 hours, followed by phase separation to give an aqueous layer. The aqueous layer was analyzed by a chiral column (Chirosil RCA) and it was confirmed that L/D ratio of 4-chlorophenylalanine is 50.1/49.9 and thus a racemization has occurred.

[Conditions for the Chiral HPLC Analysis]
Column: Chirosil RCA
Mobile phase: 10 mM HClO4 50% in MeOH
Velocity of mobile phase: 0.5 mL/min
Column temperature: 40° C.

Examples 9~10

Racemization of L-4-chlorophenylalanine

In the same manner as in Example 8, step 1) and step 2) were performed to proceed a racemization of L-4-chlorophenylalanine.

The racemization results of Examples 8~10 are shown in Table 2 below:

TABLE 2

| Examples | Reaction time | L/D ratio |
|---|---|---|
| 8 | 13 h | 50.1/49.9 |
| 9 | 15 h | 50.0/50.0 |
| 10 | 15 h | 51.1/48.9 |

Example 11

Racemization of L-leucine

1) Preparation of an Organic Layer Containing Copper Metal Complex

In dichloromethane 40 mL, 5-nitrosalicylaldehyde (3.4 g) and Aliquat 336 (12 g) were dissolved to give an organic phase. In distilled water 40 ml, racemic leucine (5.2 g), sodium hydroxide (1.75 g) and copper chloride (CuCl2) (0.6 g) were dissolved to give an aqueous phase. The organic phase and the aqueous phase were mixed and the resultant two-phase mixture was vigorously stirred for 1 hour, followed by a phase separation to obtain an organic layer containing copper metal complex.

2) Racemization

In distilled water 100 ml, L-leucine (13.3 g) and sodium hydroxide (4.8 g) were dissolved to prepare an aqueous phase, to which the organic layer obtained in the above step 1) was added. The resultant two-phase mixture was stirred at 35° C. for 15 hours, followed by phase separation to give an aqueous layer. The aqueous layer was analyzed by a chiral column (Sumichiral OA-5000) and it was confirmed that L/D ratio of leucine is 51.0/49.0 and thus a racemization has been carried out.

[Conditions for the Chiral HPLC Analysis]
Column: Sumichiral OA-5000
Mobile phase: 10% ACN in 2 mM CuSO4
Velocity of mobile phase: 1.0 mL/min
Column temperature: 30° C.

INDUSTRIAL APPLICABILITY

The method of the present invention can be industrially utilized in the production of an optically active α-amino acid which can be used as a raw material or intermediate in the field of pharmaceuticals, agriculture and fine chemistry.

What is claimed is:

1. A method for α-amino acid racemization, comprising contacting an organic phase comprising a copper metal complex of Formula 1 with a basic aqueous phase comprising an optically active α-amino acid in the presence of a phase transfer catalyst

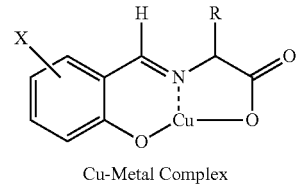

[Formula 1]

Cu-Metal Complex wherein, X represents a hydrogen, a halogen atom, an alkyl group having from 1 to 4 carbon atoms, an alkoxy group having from 1 to 4 carbon atoms or a nitro group.

2. The method according claim 1, wherein said phase transfer catalyst is a tetraalkylammonium salt ($R_4N^+X^-$) or tetraalkylphosphonium salt ($R_4P^+X^-$), wherein R independently represents an alkyl group having 1-20 carbon atoms, a substituted or unsubstituted phenyl group or a substituted or unsubstituted benzyl group, and X represents Cl, Br, I or OH.

3. The method according claim 1, wherein said phase transfer catalyst is Aliquat 336.

4. The method according claim 1, wherein said amino acid is phenylalanine, a substituted phenylalanine, leucine, alanine or methionine.

5. The method according claim 1, comprising:
(A) preparing an organic phase comprising said copper metal complex and said phase transfer catalyst,
(B) preparing a basic aqueous phase comprising an optically active α-amino acid and an alkaline compound, and
(C) racemizing a two-phase mixture obtained by combining the organic phase and the aqueous phase at a temperature 10 to 80° C.

6. The method according claim 5, further comprising:
(D) allowing the two-phase mixture resultant from said step (C) to stand and separate into an organic phase and an aqueous phase, and
(F) employing the separated organic phase obtained in step (D) as an organic phase again in step (A).

7. The method according claim 5, wherein said copper metal complex and phase transfer catalyst are obtained by:
(a-1) preparing an organic phase comprising salicylaldehyde and a phase transfer catalyst,
(a-2) preparing a basic aqueous phase comprising α-amino acid, an alkali compound and a copper salt compound, and
(a-3) stirring a two-phase mixture of the organic phase and the basic aqueous phase and then allowing it to stand to separate an organic phase and an aqueous phase.

* * * * *